(12) United States Patent
Alzaidi

(10) Patent No.: US 8,767,912 B1
(45) Date of Patent: Jul. 1, 2014

(54) SYSTEM FOR INSPECTION AND IMAGING OF INSULATED PIPES AND VESSELS USING BACKSCATTERED RADIATION AND X-RAY FLUORESCENCE

(71) Applicant: King Abdulaziz University, Jeddah (SA)

(72) Inventor: Samir Abdul-Majid Alzaidi, Christchurch (NZ)

(73) Assignee: King Abdulaziz University, Jeddah (SA)

( * ) Notice: Subject to any disclaimer, the term of this patent is extended or adjusted under 35 U.S.C. 154(b) by 38 days.

(21) Appl. No.: 13/859,636

(22) Filed: Apr. 9, 2013

(51) Int. Cl.
*G01B 15/08* (2006.01)
*G01N 23/203* (2006.01)
*H05G 1/02* (2006.01)
*G01V 5/12* (2006.01)

(52) U.S. Cl.
USPC ................ 378/59; 378/46; 378/193; 250/268

(58) Field of Classification Search
USPC ............. 378/1, 44–46, 48–50, 62, 63, 70, 82, 378/83, 86–90, 120, 147, 193, 203, 210, 378/59; 250/253, 256, 261, 264, 268, 250/269.1, 269.2, 269.3, 269.7, 265, 266, 3, 250/58.1, 360.1, 370.01, 370.06, 370.08, 250/370.09, 370.1, 370.13, 71, 393–395, 250/491.1, 493.1, 494.1, 496.1, 503.1, 250/505.1, 506.1, 522.1, 526
See application file for complete search history.

(56) References Cited

U.S. PATENT DOCUMENTS

| 2,478,842 | A | * | 8/1949 | Schwartz et al. | ................ | 378/58 |
| 3,497,691 | A | * | 2/1970 | Chen | ................ | 378/90 |
| 3,539,808 | A | * | 11/1970 | Hahn | ................ | 250/308 |
| 4,047,029 | A | * | 9/1977 | Allport | ................ | 378/90 |

(Continued)

FOREIGN PATENT DOCUMENTS

| WO | WO 9322661 A1 | 11/1993 |
| WO | WO 9733141 A1 | 9/1997 |
| WO | WO 9914581 A1 | 3/1999 |

OTHER PUBLICATIONS

Samir Abdul-Majid and Ahmed Balamesh, "Imaging Corrosion Under Insulation by Gamma Ray Backscattering Method", 18th World Conference on Nondestructive Testing, Apr. 16-20, 2012, Durban, South Africa.

(Continued)

*Primary Examiner* — Anastasia Midkiff
(74) *Attorney, Agent, or Firm* — Richard C Litman

(57) ABSTRACT

The system for the inspection and imaging of insulated pipes and vessels using backscattered gamma radiation and X-ray fluorescence includes a frame having a pair of coaxial rings adapted for coaxial mounting about the insulated pipe, vessel or the like. A pair of rotating supports are rotatably mounted within the pair rings for driven rotation thereof. A plurality of horizontal supports are secured to, and extend between, the pair of rotating supports such that each of the horizontal supports extends along a direction parallel to an axis of the insulated pipe. A plurality of inspection modules are slidably mounted to the horizontal supports. Each inspection module includes at least one radiation source, an X-ray fluorescence detector and a backscattered gamma radiation detector. The plurality of inspection modules are linearly translated along the axial direction of the pipe, and also circumferentially rotated therearound for simultaneous, three-dimensional inspection of the pipe body.

20 Claims, 9 Drawing Sheets

(56) References Cited

U.S. PATENT DOCUMENTS

| | | | |
|---|---|---|---|
| 4,229,652 A * | 10/1980 | Weinstock et al. | 850/29 |
| 4,580,053 A | 4/1986 | Snyder | |
| 5,195,117 A | 3/1993 | Ong | |
| 5,698,854 A * | 12/1997 | Gupta | 250/358.1 |
| 5,970,116 A | 10/1999 | Dueholm et al. | |
| 6,252,930 B1 | 6/2001 | MacKenzie | |
| 6,421,418 B1 | 7/2002 | Schulte | |
| 6,556,653 B2 * | 4/2003 | Hussein | 378/90 |
| 6,895,074 B2 | 5/2005 | Benedetti | |
| 7,203,276 B2 * | 4/2007 | Arsenault et al. | 378/87 |
| 7,872,222 B1 * | 1/2011 | Dep et al. | 250/253 |
| 8,073,106 B2 * | 12/2011 | Wallace | 378/89 |

OTHER PUBLICATIONS

Samir Abdul-Majid et al., "Use of Gamma Ray Back Scattering Method for Inspection of Corrosion under Insulation," 3rd MENDT—Middle East Testing Conference and Exhibition, Nov. 27-30, 2005, 8 pages, published online at www.ndt.net.

* cited by examiner

SYSTEM FOR INSPECTION AND IMAGING OF INSULATED PIPES AND VESSELS USING BACKSCATTERED RADIATION AND X-RAY FLUORESCENCE

BACKGROUND OF THE INVENTION

1. Field of the Invention

The present invention relates to the inspection of insulated pipes, vessels and the like, and particularly to a system for the inspection of insulated pipes and vessels using backscattered radiation and X-ray fluorescence.

2. Description of the Related Art

Large insulated pipes are often found in numerous industries, such as in gas producing plants for carrying both liquids and gas, particularly for maintaining fluids under low temperatures, in electrical plants for high temperature applications, and in many other industries where both high and low temperature fluids are utilized. The insulation around the pipes is necessary for maintaining relatively low and high fluid temperatures. The insulation layer on the pipes in these plants, as well as in various other industrial applications, is typically at least several centimeters thick, thus making it extremely difficult to inspect the pipe bodies for corrosion. Plant production must be stopped for interior visual inspection of the pipe walls, and removal of the outer insulation for exterior visual inspection not only requires a great deal of time and expense, but can be detrimental to the pipe itself, since ice forms on the exposed pipe surface for low temperature applications, along with potentially dangerous increases of pressure in the interior, and since heat is lost in high temperature applications. Additionally, such visual inspections of the pipe exterior will not indicate corrosion formed on the interior of the pipe. As noted above, conventional interior inspection would require a shutdown of the plant processes. In addition to visual inspection, other techniques, such as ultrasonic inspection, have been tried, but such methods have typically been found to be difficult to implement due to the inability of the ultrasonic probe to make contact with the pipe or tank wall due to the insulation. Further, ultrasonic methods typically do not work well in the high temperature environments of fluid-carrying pipes and the like.

Although direct radiography allows for inspection of such pipes without the removal of the insulation layer, direct radiography has a number of drawbacks. As illustrated in FIG. 2, in conventional direct radiographic inspection, a radiation source 100 is positioned on one side of the object under inspection and radiographic film or an image plate is positioned opposite the source 100. In the specific application of insulated pipe inspection, the radiation source 100 emits radiation 102, which may be X-rays, gamma rays or the like, which pass through an insulated pipe, which includes a conventional pipe 106 carrying some sort of fluid 112, the pipe 106 being surrounded by an outer annular insulation layer 104. A radiographic film or image plate 110 is placed to the other side of the pipe for imaging corrosion 108 that may be formed on the pipe 106. A wide variety of other techniques involving radiographic imaging have been used, such as insertion of radioisotopes within the pipe for use with an external detector, an internal floating camera, etc. Such methods, though, require complete plant shutdown and are typically highly impractical and expensive to implement.

The attenuation of X-ray and gamma ray radiation is very high in large bodies, such as in the exemplary insulated pipe of FIG. 2. If the object is very large, not enough radiation reaches the film or image plate 110 due to attenuation in the fluid 112 and in the metal wall (typically iron or iron-based materials) wall of the pipe 106. Additionally, as illustrated in FIG. 2, a relatively wide beam must be used, allowing for inspection of all sides of the pipe, which is often not possible for very large pipes or tanks. If a linear accelerator or cyclotron is used as the radiation source, such a wide beam is often impossible to produce. Further, such equipment cannot be used if there is no accessible space available on one side of the object.

Further, due to the use of the single source, all sides of the pipe are imaged at the same time. This often creates confusion about the actual location of corrosion 108, since the image produced on the plate 110 is two-dimensional.

Gamma ray or X-ray backscattering are known techniques for determining metal thickness, such as in measuring the thickness of corroded portions of metal bodies. In backscattered radiation imaging, a gamma ray or X-ray beam is projected incident on the wall of the pipe. Its energy can be selected to be great enough that attenuation in the insulator is insignificant. As gamma rays or X-rays penetrate the pipe, the radiation undergoes attenuation, the radiation intensity decreasing exponentially with wall thickness. The magnitude of attenuation depends on the energy of the incident radiation and the nature of the material. Backscattering takes place from within layers of the wall by Compton interactions. The backscattered radiation undergoes higher attenuation in its path back to the detector or the film, since its energy is lower than that of the primary incident radiation. The radiation will, therefore, undergo double attenuation.

In X-ray fluorescence (XRF) imaging, the incident radiation interacts with the pipe material, followed by emission of XRF radiation. This type of X-ray is characteristic of wall materials. Most pipes and vessels of the type of interest have walls made from iron or iron-based materials. The emitted X-rays have relatively small energies, typically around 7 keV. Additional detectors having high sensitivity for low energy radiation may be used if the first detector is not sensitive enough. It is generally preferable to use a radiation source that emits low energy in order to have a high level of reaction with the object materials. Because of the low energy of the XRF radiation, it is emitted from the surface of the object wall, thus it can image the outer surface of the object. This makes XRF desirable for insulated pipe inspection, since corrosion takes place on the outer surface of the pipe due to moisture trapped under the insulating layer, as well as on the wall body, which causes changes in thickness.

In FIG. 3, a radioactive source 100 emits one or a few well-defined gamma rays. The radiation 102 that is incident on the pipe wall 106 (and passes through insulating layer 104) is collimated by a collimator 114. A portion of the incident radiation 102 will backscatter due to Compton interactions, and a portion will also produce XRF radiation. The backscattered radiation 124 is measured by a gamma ray detector 118 (typically including a spectrometer, such as a NaI (Tl) scintillation detector), while the XRF radiation 120 is measured by a low energy X-ray detector 116, such as a CdTe, Si(Li) or $HgI_2$ detector. Typically, both types of detectors must be utilized, as the NaI (Tl) scintillation detector does not properly detect X-rays and, similarly, the CdTe, Si(Li) or $HgI_2$ detector is ineffective in detecting gamma rays. Further, it can be easily seen that the backscattered radiation 124 is received by detector 118 in a wide variety of angles, rather than being received at a desired angle.

Backscattered radiation, measured at a fixed angle $\theta$, and the XRF each give defined peaks when measured with energy analyzers, such as conventional multichannel analyzers. Counting windows can be selected to measure backscattered radiation peaks and XRF radiation. Single detectors, as illustrated in FIG. 3, though, are limited in their functionality, due to limitations in positioning, fixed degrees of angular measurement, and limited views of only portions of a pipe under inspection. It would be desirable to provide a scanning system capable of constructing an entire pipe wall image. It is further necessary to provide proper imaging hardware and software for converting counts into images using computer imaging programs, such as LabVIEW®, for example, coupled with scanning.

Thus, a system for the inspection and imaging of insulated pipes and vessels using both backscattered gamma radiation and X-ray fluorescence solving the aforementioned problems is desired.

SUMMARY OF THE INVENTION

The system for the inspection, scanning and imaging of insulated pipes and vessels using backscattered radiation and X-ray fluorescence uses multiple inspection modules for simultaneously scanning, imaging and inspecting an insulated pipe. Imaging is performed using both Compton backscattered radiation and X-ray fluorescence. The Compton radiation is used for thickness imaging and the X-ray fluorescence is used for surface imaging. The system includes a frame having a lower base portion and an upper portion. The upper portion has a pair of spaced apart, coaxial rings adapted for coaxial mounting about the insulated pipe. A pair of rotating supports are respectively rotatably mounted within the pair of spaced apart, coaxial rings of the frame for driven rotation thereof with respect to the frame. A plurality of horizontal supports are secured to, and extend between, the pair of rotating supports such that each of the horizontal supports extends along a direction parallel to an axis of the insulated pipe.

A plurality of inspection modules are slidably mounted to the plurality of horizontal supports. Each inspection module includes at least one radiation source, an X-ray fluorescence detector and a backscattered gamma radiation detector. Preferably, each inspection module is adjustably mounted on the corresponding one of the plurality of horizontal supports such that a radial height between the inspection module and an outer surface of the insulated pipe is adjustable. Adjacent inspection modules may be axially staggered with respect to one another. The inspection modules are linearly translated along the axial direction of the pipe, and also circumferentially rotated around the pipe for simultaneous, three-dimensional inspection of the pipe body. The inspection modules are in communication with a multi-channel analyzer, where a selected window of the multi-channel analyzer allows for selection of, and analysis on, a desired part of the spectrum. As a further alternative, multiple radiation sources may be utilized for producing multiple images of a single object to be inspected and imaged.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
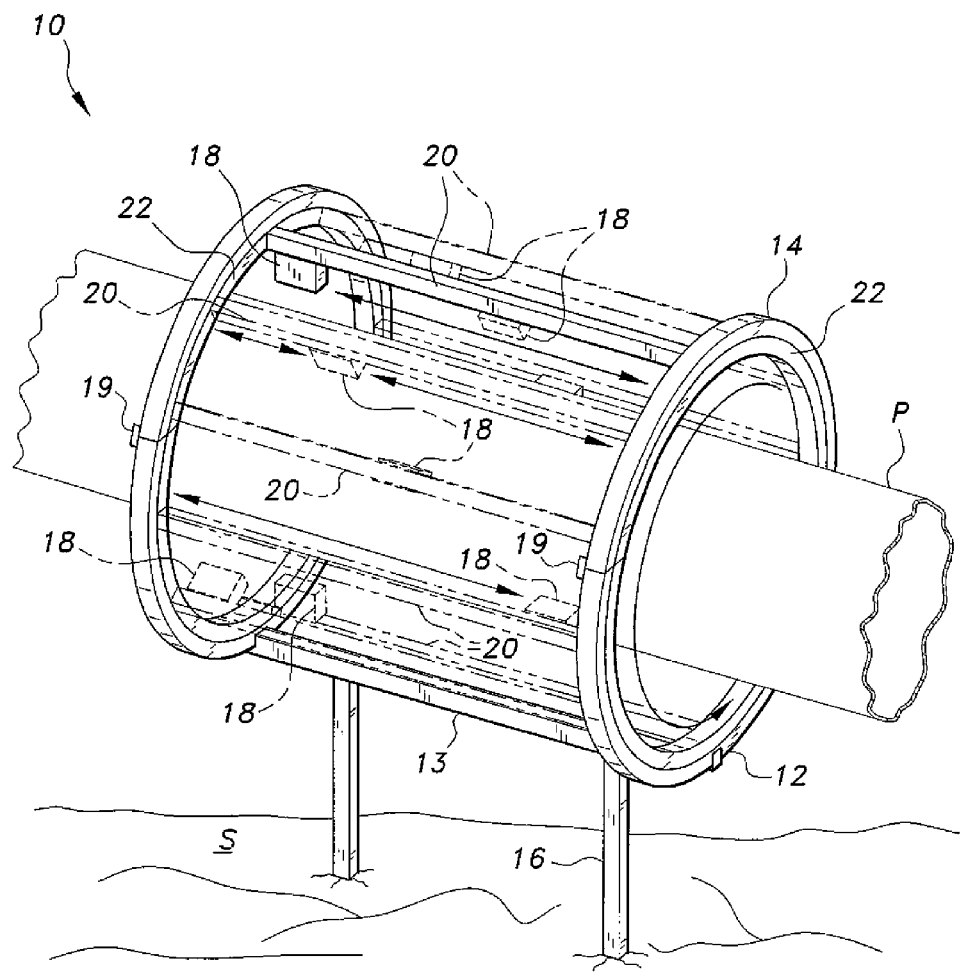
FIG. 1 is an environmental, perspective view of a system for the inspection and imaging of insulated pipes and vessels using backscattered radiation and X-ray fluorescence according to the present invention.
Figure 2:
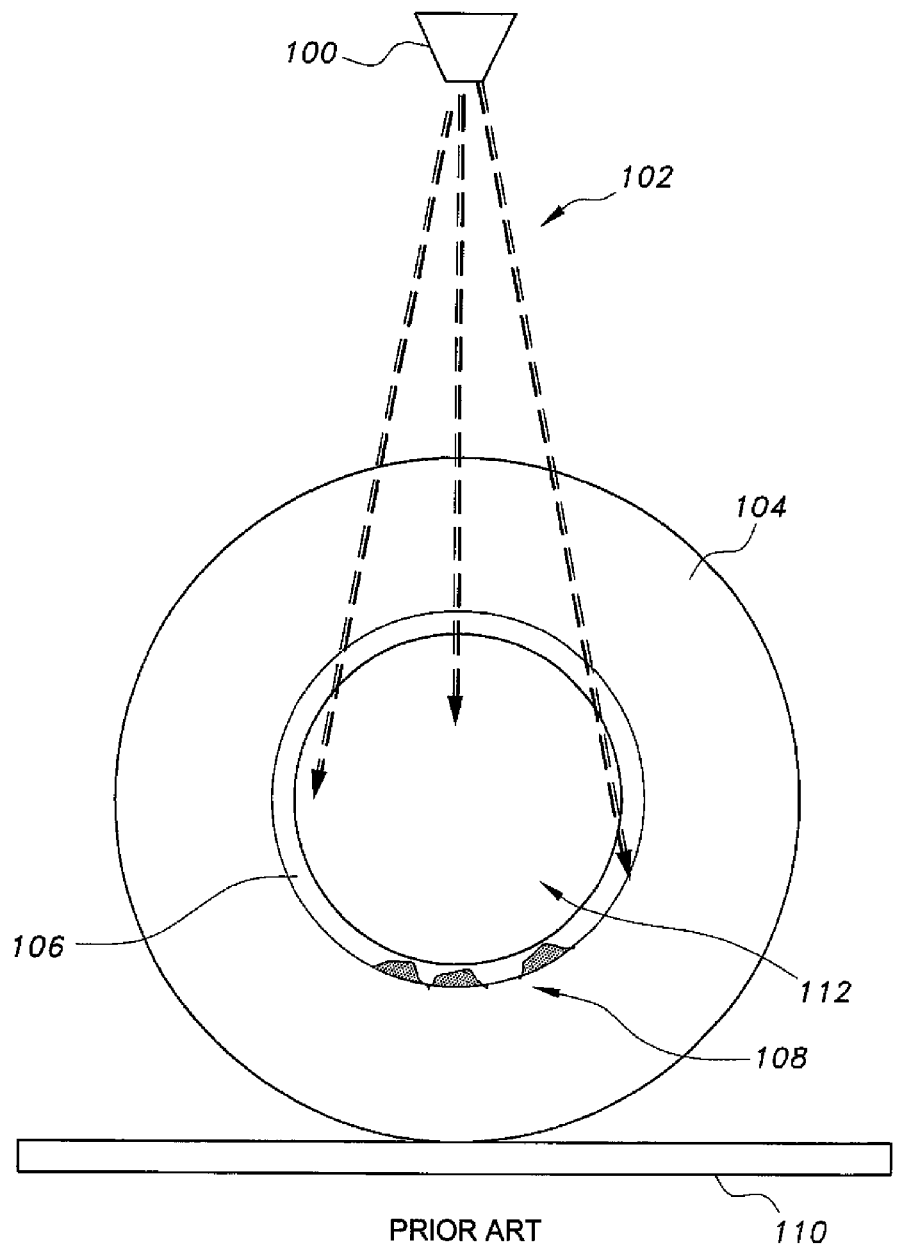
FIG. 2 diagrammatically illustrates a prior art approach to direct radiographic inspection of a pipe.

As shown in FIG. 1, the system for the inspection and imaging of insulated pipes and vessels using backscattered radiation and X-ray fluorescence, designated as system 10 in the drawings, allows for the rapid and accurate inspection and imaging of insulated pipes, vessels and the like using both backscattered gamma radiation and X-ray fluorescence. Although the following description illustrates the system as applied to insulated pipes, it will be understood that the same system may be applied to insulated tanks, heat exchangers, and other insulated objects. The present system allows for multiple inspection modules 18 to be mounted about the periphery of pipe P for simultaneous inspection thereof. In FIG. 1, for exemplary and illustrative purposes, only eight such inspection modules 18 are illustrated. However, it should be understood that any desired number of modules 18 may be used. The plurality of modules 18 preferably encircle the pipe P. It should be further understood that the insulated pipe P is shown for exemplary purposes only, and that the overall dimensions and configuration of the system 10 may vary, depending upon the particular configuration of the pipe P.

The system 10 includes a frame 12 having an upper portion 14 and a base 16. The base 16 is adapted for mounting on the ground or other surface S. It should be understood that the overall configuration of the base 16 may vary, depending upon the environment in which the pipe P is located, and the base 16 in FIG. 1 is shown for exemplary purposes only. Further, the base 16 may have an adjustable height and may be movable. The upper portion 14 of the frame 12 includes a pair of spaced apart rings, which are supported by a horizontal mount 13 and are mounted about the pipe P such that the pipe P and the rings of the upper portion 14 are substantially coaxial. Mounted within each ring of the upper portion 14 is a rotating support 22. It should be understood that the base 16 may be removed if the pipe allows system 10 to be directly seated thereon and secured thereto. As shown in FIG. 1, each ring may be divided into two semi-circular sections, joined together by a lock or seal 19, allowing the upper portion 14 to be fitted about a long pipe P or the like.

Figure 4:
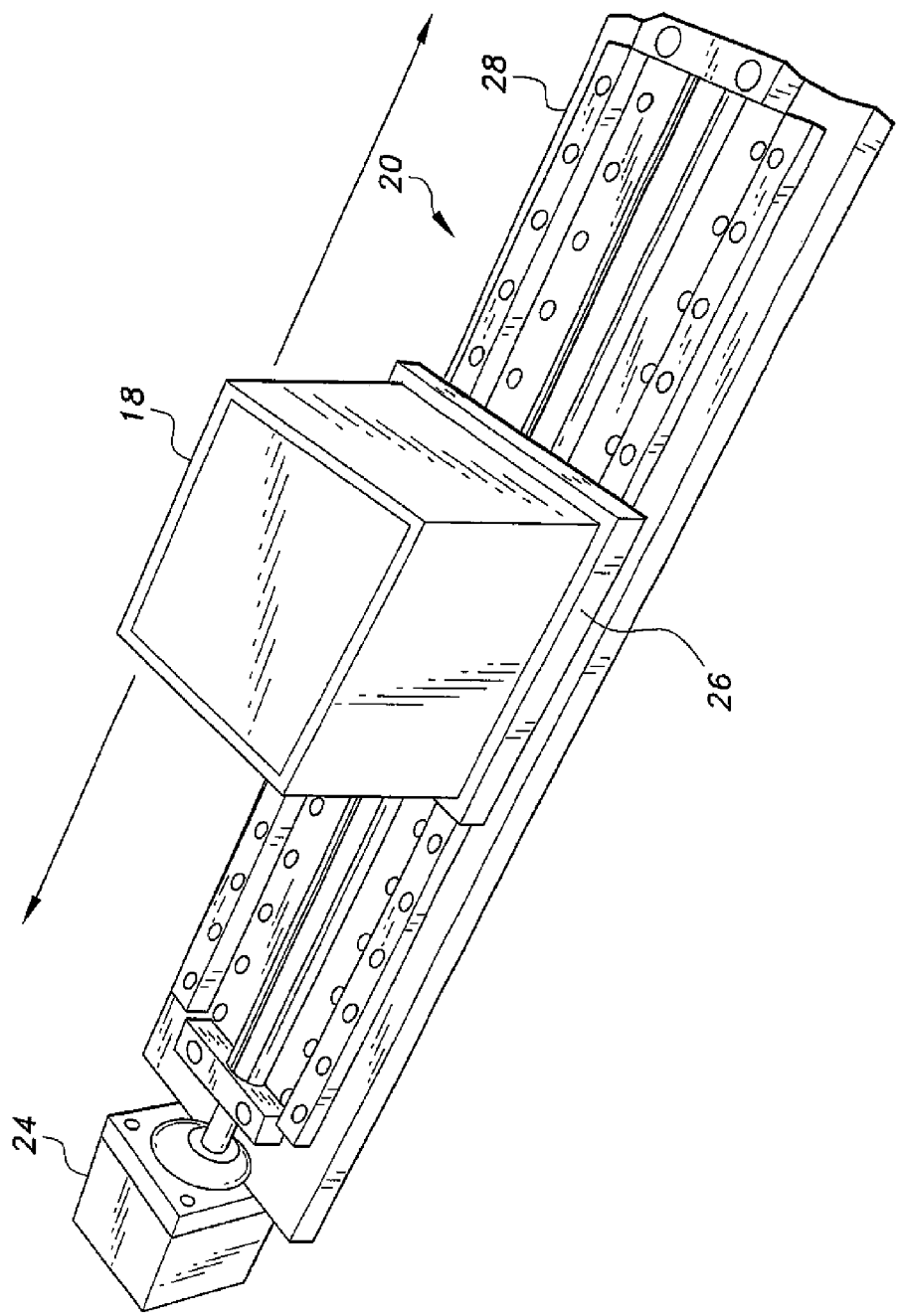
FIG. 4 is a perspective view of an inspection module and linear slide of the system of FIG. 1.

Extending between the rotating supports 22, which are rotatably mounted in the rings of the upper portion 14, are a plurality of horizontal supports 20, each arranged to be substantially parallel with the axis of the pipe P. Each inspection module 18 is slidably mounted to a respective one of the horizontal supports 20. Each horizontal support 20 is preferably a linear slide, allowing for controlled linear translation of the respective inspection module 18. Linear slides, such as the exemplary linear slide 20 shown in FIG. 4, are well known in the art (sometimes also referred to as "linear stages"). The exemplary linear slide 20 of FIG. 4 includes a base 28 and a platform 26 slidably mounted thereon. The platform 26 is adapted for fixed attachment of the module 18 thereto. Controlled sliding of the platform 26 with respect to the base 28 is driven by an adjustable, controllable servo-motor 24 or the like. It should be understood that any suitable method of controlled, linear translation of the inspection modules 18 may be used, such as linear actuators or the like.

Figure 3:
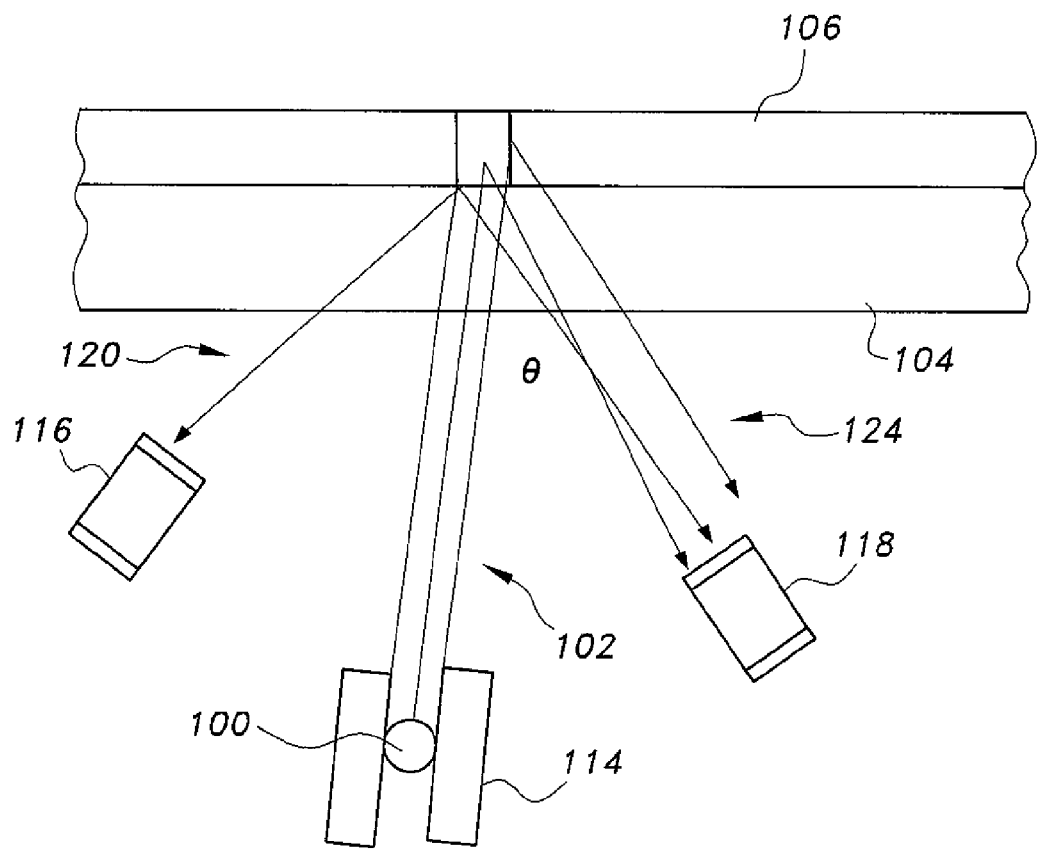
FIG. 3 diagrammatically illustrates a prior art technique for inspection by backscattered radiation.
Figure 8:
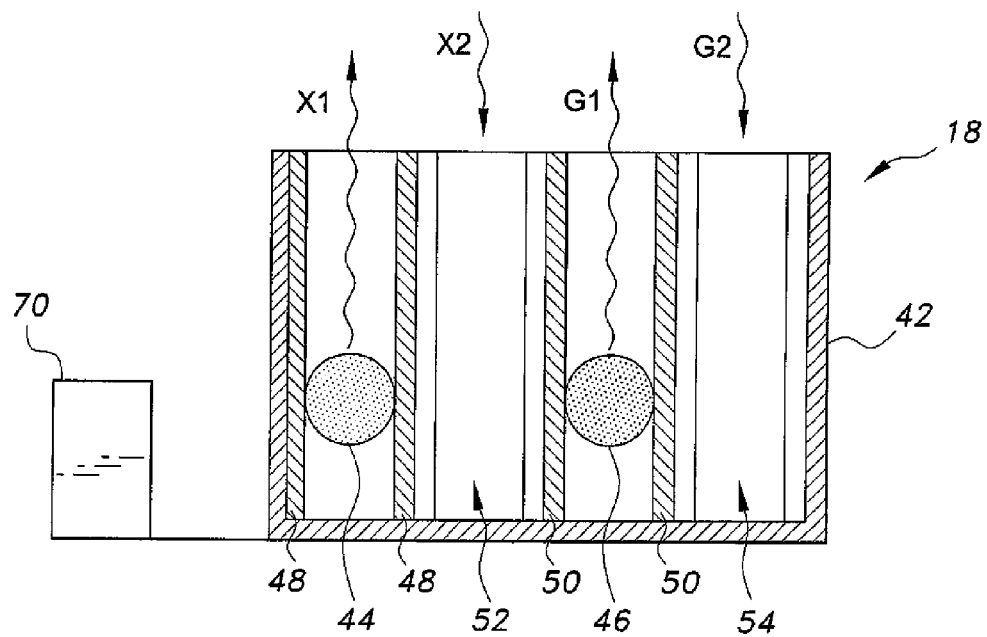
FIG. 8 is a side view in section of the inspection module of the system of FIG. 1.

FIG. 8 illustrates an inspection module 18, which detects both X-ray fluorescence and backscattered gamma radiation used for inspection of the pipe P, as described above in reference to FIG. 3. In FIG. 8, both an X-ray source 44 and a gamma ray source 46 are shown, mounted within respective collimators 48, 50, although it should be understood that a single source may be used (as in the example of FIG. 3), or both sources may be positioned together within a single collimation tube or the like. In addition to the sources 44, 46, the module 18 preferably includes a radiation-shielded housing 42, an X-ray fluorescence detector 52, a backscattered gamma radiation detector 54, and an associated conventional nuclear electronics, such as a multi-channel analyzer 70 or the like, as is well known in radiation detection methods for detecting gamma or X-ray radiation peaks. The operation of the inspection module 18 is similar to that discussed above with respect to FIG. 3, although the sources 44, 46 and the detectors 52, 54 are all mounted within a single, radiation-shielded module. The X-ray source 44 emits X-rays X1, and the gamma radiation source emits gamma rays G1. The received XRF signal X2 is detected by the X-ray detector 52, and the backscattered gamma radiation G2 is detected by the backscattered gamma radiation detector 54.

Figure 5:
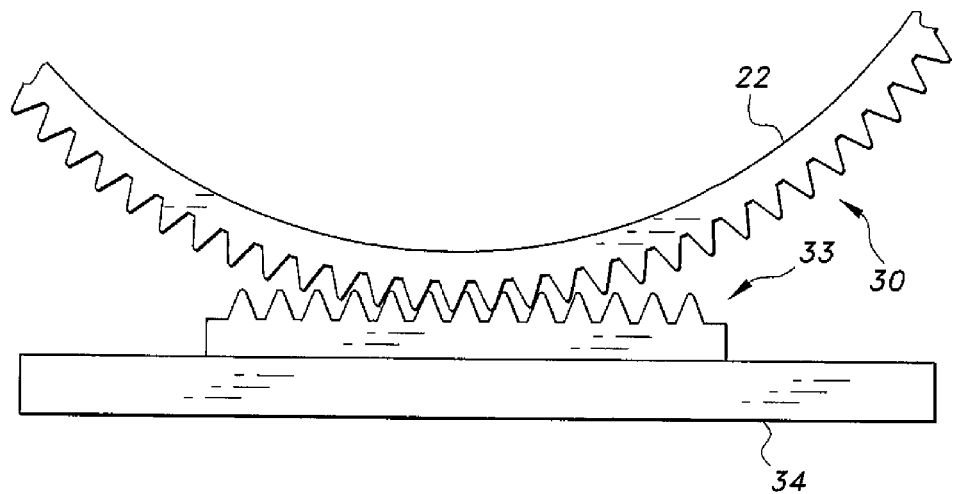
FIG. 5 is a partial side view of a rotational drive of the system of the system of FIG. 1.
Figure 6:
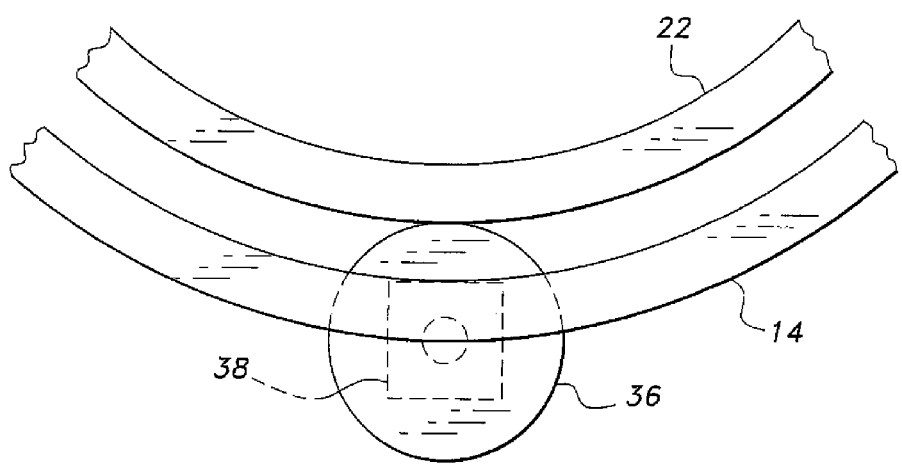
FIG. 6 is a partial side view of an alternative embodiment of the rotational drive of the system of FIG. 1.

In addition to the linear sliding of modules 18, allowing lengthwise inspection coverage of pipe P, each horizontal support 20 and its respective module 18 controllably rotates about the circumference of pipe P. As noted above, each horizontal support 20 extends between the pair of rotating supports 22, which are rotatably mounted within the rings of the upper portion 14 of the frame 12. The rotating supports 22 rotate together simultaneously to maintain the horizontal supports 20 in a parallel orientation with the axis of pipe P. Rotation may be driven by any suitable method. For example, as shown in FIG. 5, a linear slide 34 (similar to linear slides 20) may be mounted to the frame 12, and a linear gear 33 may be mounted on the sliding platform thereof. The linear gear 33 contacts a toothed outer edge 30 of a corresponding one of rotating supports 22, so that linear translation of the linear gear 33 causes the corresponding rotating support 22 to rotate. Alternatively, as shown in FIG. 6, one or more wheels 36 may be mounted to a ring of the upper portion 14 of the frame 12, and each wheel 36 may make frictional contact with an outer edge of a corresponding rotating support 22. Each wheel 36 may be driven by a motor 38 or the like, thus driving rotation of the corresponding rotating support 22. As noted above, any suitable method for driving rotation of the rotating supports 22 may be utilized.

Figure 7:
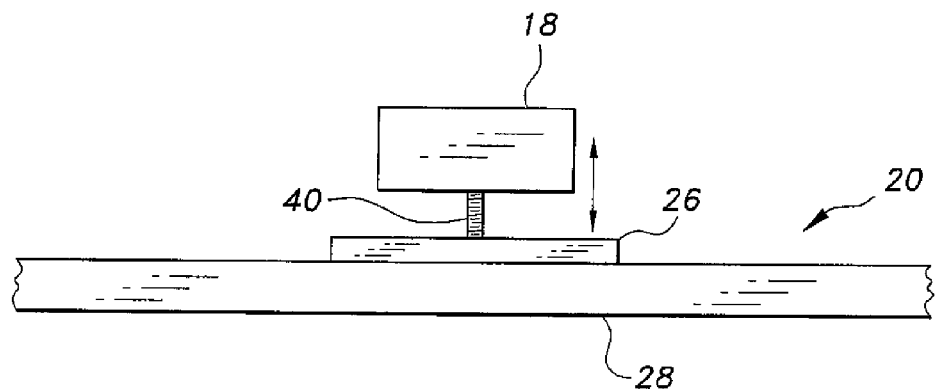
FIG. 7 is a side view of an alternative embodiment of the inspection module and linear slide of FIG. 4.

Further, as shown in FIG. 7, fine control of the height (with respect to the outer surface of the pipe P) of each inspection module 18 may be adjusted. Each inspection module 18 is adjustably mounted on its respective platform 26 by a threaded screw 40 or the like. This allows the radial distance between the inspection module 18 and the pipe surface to be adjusted, either manually or under automatic control.

Thus, in the present system 10, the linear, axial position of each inspection module 18 may be adjustably controlled (via linear translation of each inspection module 18 with respect to its corresponding horizontal support 20), the angular position of each inspection module 18 may be adjustably controlled (via controlled rotation of rotating supports 22 with respect to frame 12), and the height (i.e., radial distance) of each inspection module 18 with respect to the outer surface of pipe P may be adjustably controlled (by fine adjustment of threaded screw 40).

In use, the inspection modules 18 preferably all linearly translate at once, in sync. This allows for rapid inspection of a wide portion of the pipe P simultaneously. As noted above, only eight such inspection modules 18, covering only one area of pipe P, are shown in FIG. 1. However, it should be understood that any desired number of modules 18 may be used at once. The modules 18 may completely circumferentially cover the perimeter of pipe P. However, it should be noted that the circumferential distance between adjacent inspection modules 18 should be large enough so that scattered radiation from one inspection module 18 does not affect detection by other inspection modules 18.

Although the modules 18 are shown spaced apart from the outer surface of the pipe P, it should be understood that this is shown for illustrative purposes only. Preferably, the radial height above the outer surface of the pipe P is very small, such that each module 18 almost touches the outer surface of the pipe P.

As shown in FIG. 1, the linear, axial position of modules 18 is staggered. Although the modules 18 preferably move together, in sync, each module 18 may be individually controlled and driven, allowing independent movement of individual modules, if desired. In order to increase accuracy (i.e., decrease pixel size), the incident beam is made sharper (by narrowing the collimation tube of incident or scattered radiation) and each incremental linear translation is made smaller. Each module 18 generates its own image (i.e., a line image) when it axially translates. Following a full scan, the individual line images are combined to form a full surface image of the pipe P. Radiation counts collected by the detector are acquired by a computer using imaging programs, such as LabVIEW®, produced by the National Instruments® Corporation of Delaware.

As noted above, with reference to FIG. 8, a single radiation source may be used, although it is preferable to use multiple radiation sources. Additionally, although shown in two separate collimators, both sources may be disposed within a single collimator. Any suitable high energy or intermediate energy gamma source may be used, such as $^{137}$Cs (0.662 MeV) or $^{60}$Co (1.173, 1.332 MeV), or a combination of the two. Both of these materials have energy suitable for penetration of the pipe wall and are capable of providing data on the wall thickness. Similarly, any suitable low energy X-ray source may be used, such as $^{241}$Am (0.0595 MeV). The emitted XRF from iron is about 7 keV. The probability of interaction is higher if the incident energy is closer to the emitted XRF energy.

Figure 11:
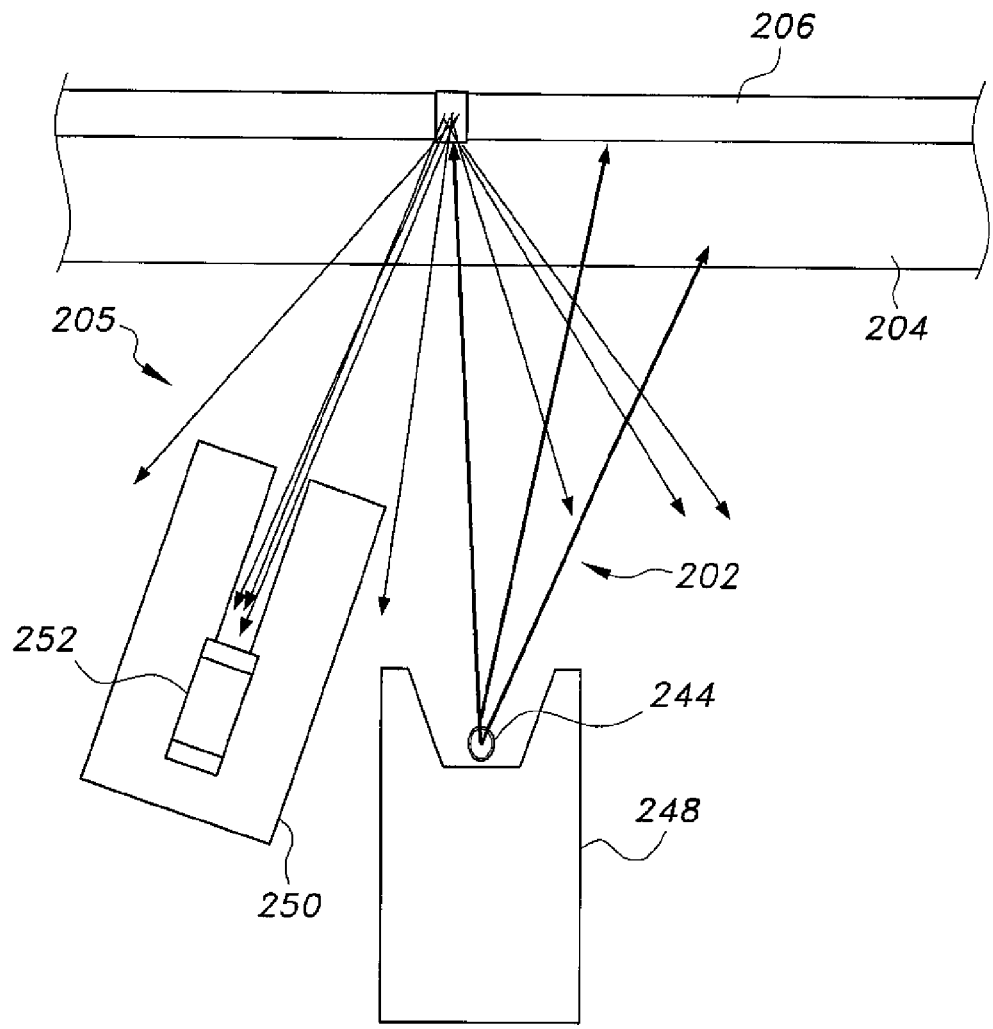
FIG. 11 diagrammatically illustrates collimation of backscattered radiation in the system for the inspection and imaging of insulated pipes and vessels using backscattered radiation and X-ray fluorescence.

Any suitable type of backscattered gamma radiation detector 54 may be used, such as a NaI(Tl) scintillation detector or the like. Similarly, any suitable XRF detector 52 may be used, such as a CdTe detector, which has very low sensitivity for measuring energy higher than 100 keV. FIG. 11 illustrates, conceptually, the advantage of collimating not only the emitted radiation from source 244 (with collimator 248) but the backscattered radiation received by detector 252 (and collimated by collimator 250). In FIG. 11, inspection of a pipe 206 with insulating layer 204 is being performed, similar to that shown in FIG. 3. However, both the emitted radiation 202 and the backscattered radiation 205 are both collimated. As shown, highly accurate measurements, at a desired angle, can be made by collimating the backscattered radiation 205, as shown diagrammatically in FIG. 11, and as implemented in the module of FIG. 8.

As noted above with reference to FIG. 8, analyzer 70 is preferably a multi-channel analyzer. As is well known, the multi-channel, spectrum analyzer shows the energy of radiation. Each primary, or scattered at a specific angle, gamma energy appears as a peak on the analyzer screen. A specific window can be chosen to take counts under selected channels; i.e., under the peak. In the example shown in FIG. 9, actual multi-channel analyzer results are shown where the selected window is taken between channels 50-120 (approximately). Each channel has its own counts, and the window adds all counts in all channels (50-120 in FIG. 9).

Figure 9:
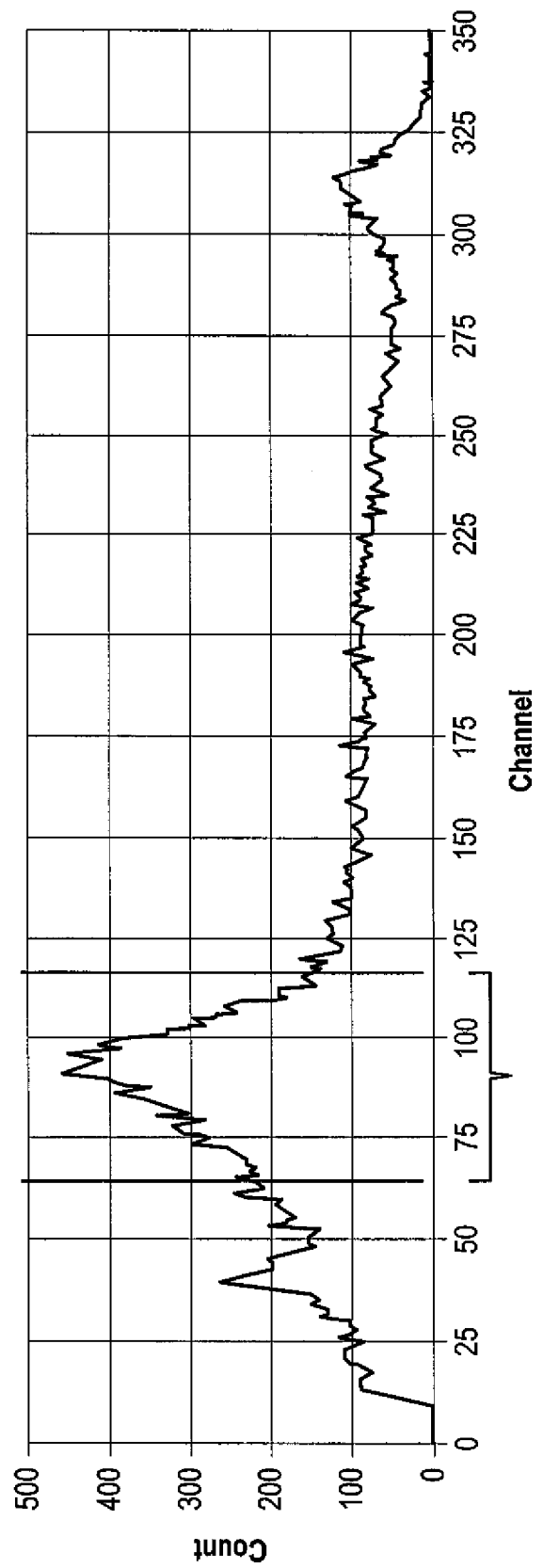
FIG. 9 illustrates exemplary multi-channel analyzer output for the system for the inspection and imaging of insulated pipes and vessels using backscattered radiation and X-ray fluorescence according to the present invention.

The total counts under the peak (i.e., in the window) are proportional to the pipe wall thickness. In FIG. 9, the scattered peak (the peak on the left in FIG. 9) appears large, while the primary peak (to the right in FIG. 9) appears small. This is because the shield between the source and the detector prevents primary radiation from reaching the detector while scattered radiation reaches the detector directly.

Figure 10:
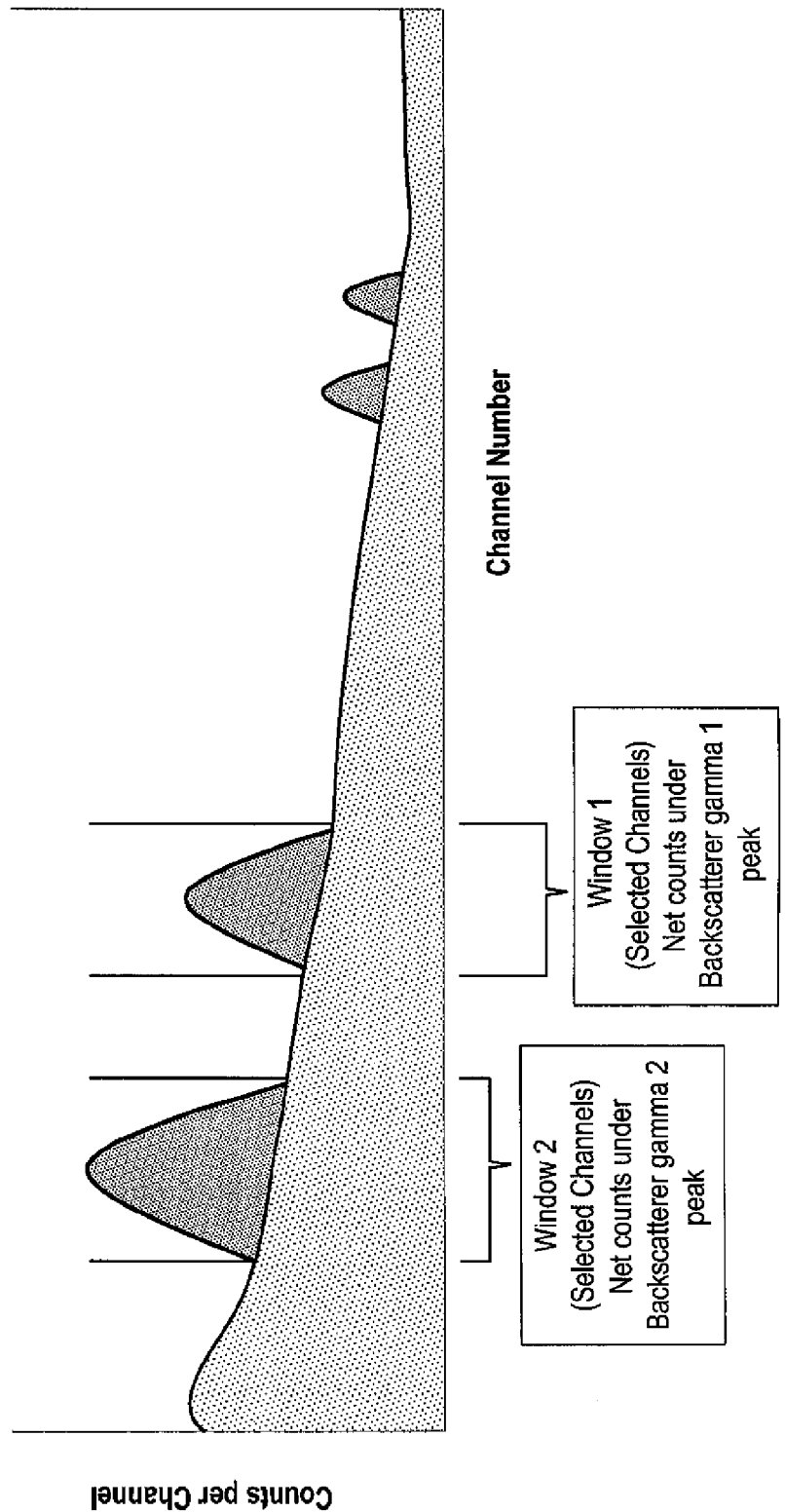
FIG. 10 illustrates an expected spectrum for an alternative embodiment of the system for the inspection and imaging of insulated pipes and vessels using backscattered radiation and X-ray fluorescence in which multiple radiation sources are utilized for double imaging of a single object.

In FIG. 10, the concept of using more than one gamma ray for backscatter (not XRF) imaging is illustrated. Assuming two gamma rays of two different energies are used, then each will produce its own backscatter peak. In FIG. 10, window two shows the net counts under backscatter gamma ray two's peak. Similarly, window one shows the net counts under backscatter gamma ray one's peak. To the right in FIG. 10 are, respectively, the peaks for primary gamma ray two and primary gamma ray one. Taking counts under each backscatter peak can produce an image. If the counts under two peaks are taken separately, then two images of the same pipe wall can be constructed. An imaging technique can be used to put the two images together to produce a better final image. The two sources can be put together or used separately. It should be understood that it is also possible to use one source that emits more than one gamma ray. The advantage of using two gamma rays of two different energies is that a better final image can be produced due to the fact that sensitivity of low gamma energy is better than the sensitivity at higher gamma energy for small thicknesses, and vice versa. Sensitivity, as used in the above, is defined as the change in total counts per change in wall thickness.

It should be understood that though shown as being applied to cylindrical pipes and the like, the present invention may be applied to any suitable type of surface. For example, the present system may be used with flat wall surfaces, such as those found in big tanks and vessels associated with insulated super-heaters and the like. Rather than a rotational system, such a system merely employs a set of linearly translating modules, which work in a manner identical to that described above.

It is to be understood that the present invention is not limited to the embodiments described above, but encompasses any and all embodiments within the scope of the following claims.

I claim:

1. A system for the inspection and imaging of insulated pipes using backscattered gamma radiation and X-ray fluorescence, comprising:
    a frame having a lower base portion and an upper portion, the upper portion having a pair of spaced apart, coaxial rings adapted for coaxial mounting about an insulated pipe, each of the rings having a rotating support rotatably mounted therein;
    means for controllably driving rotation of the rotating supports with respect to the frame;
    a plurality of horizontal supports secured to and extending between rotating supports, each of the horizontal supports extending along a direction parallel to an axis of the insulated pipe;
    a plurality of inspection modules slidably mounted on the plurality of horizontal supports, each of the inspection modules having at least one radiation source, an X-ray fluorescence detector and a gamma radiation detector;
    a multi-channel analyzer in communication with the gamma radiation detector, whereby a spectral window of interest may be selected for producing an image; and
    means for controllably translating each of the inspection modules linearly with respect to the corresponding one of the horizontal supports, whereby each said inspection module measures a surface thickness of a pipe body of the insulated pipe to determine corrosion level therein.

2. The system for the inspection and imaging of insulated pipes as recited in claim 1, wherein each said inspection module further comprises at least one collimator tube for collimating radiation generated by the at least one radiation source.

3. The system for the inspection and imaging of insulated pipes as recited in claim 2, wherein the at least one radiation source comprises an X-ray source and a gamma ray source.

4. The system for the inspection and imaging of insulated pipes as recited in claim 3, wherein the X-ray source is selected from the group consisting of 241Am, 137Cs and 60Co.

5. The system for the inspection and imaging of insulated pipes as recited in claim 1, wherein the at least one radiation source comprises a plurality of radiation sources for producing a plurality of images of an inspected area.

6. The system for the inspection and imaging of insulated pipes as recited in claim 5, wherein each said radiation source has a unique radiation energy output.

7. The system for the inspection and imaging of insulated pipes as recited in claim 1, wherein each said inspection module is adjustably mounted on the corresponding one of the plurality of horizontal supports so that a radial height between the inspection module and an outer surface of the insulated pipe is adjustable.

8. The system for the inspection and imaging of insulated pipes as recited in claim 7, wherein each said horizontal support comprises a linear slide.

9. The system for the inspection and imaging of insulated pipes as recited in claim 8, wherein each said linear slide comprises a base, a platform slidably mounted on the base, and a servo-motor, each said inspection module being mounted on a respective platform.

10. The system for the inspection and imaging of insulated pipes as recited in claim 9, further comprising a height-adjustable mount secured to each said platform for adjustable mounting of the respective one of the plurality of inspection modules thereto.

11. The system for the inspection and imaging of insulated pipes as recited in claim 1, wherein adjacent ones of the plurality of inspection modules are axially staggered with respect to one another.

12. The system for the inspection and imaging of insulated pipes as recited in claim 1, wherein each said inspection module further comprises at least one collimator tube for collimating backscattered radiation.

13. A system for inspection of an insulated structure for corrosion beneath the insulation, comprising:
- at least one gamma ray radiation source;
- at least one detector positioned to detect backscatter radiation from a beam of gamma ray radiation reflected from the insulated structure;
- a multi-channel analyzer connected to the at least one detector, the analyzer having a display for displaying gamma peaks and means for selecting a window confined to single scatter radiation;
- a frame having a lower base portion and an upper portion, the upper portion being adapted for coaxial mounting about an insulated structure, and having a rotating support rotatably mounted therein;
- means for rotating each support of the upper portion of the frame with respect to the lower base portion of the frame; and
- a plurality of horizontal supports secured to and extending between rotating supports;
- whereby the system is adapted for detecting corrosion beneath the insulation and in the thickness of the insulated structure.

14. The system for inspection of an insulated structure according to claim 13, wherein said at least one radiation source comprises a collimator for emitting a narrow beam of gamma radiation.

15. The system for inspection of an insulated structure according to claim 14, wherein said at least one detector comprises a collimator for collimating the reflected backscatter radiation received at the detector.

16. The system for inspection of an insulated structure according to claim 13, wherein said at least one radiation source comprises a single radiation source having means for emitting a plurality of gamma rays of different energy level, whereby multiple spectral images of a common location may be displayed on said analyzer.

17. The system for inspection of an insulated structure according to claim 13, wherein said at least one radiation source comprises a plurality of radiation sources, the sources emitting a plurality of gamma rays at different energy levels at a common location, whereby multiple spectral images of the common location may be displayed on said analyzer.

18. The system for inspection of an insulated structure according to claim 13, wherein said at least one detector comprises a collimator for collimating the reflected backscatter radiation received at the detector.

19. The system for inspection of an insulated structure according to claim 13, wherein said at least one source and said at least one detector comprises a plurality of sources and a plurality of detectors, each of the sources being paired with a corresponding one of the detectors to define a plurality of monitoring stations, the monitoring stations being spaced apart and focused at a common location of the insulated structures for forming a plurality of partial spectral images of the common location at said analyzer.

20. The system for inspection of an insulated structure according to claim 13, further comprising:
- a source of X-ray fluorescence radiation, the at least one gamma ray radiation source and the source of X-ray fluorescence radiation being configured for emitting radiation beams at a common location on the insulated structure; and
- an X-ray fluorescence detector positioned to detect backscatter radiation from a beam of X-ray fluorescent radiation emitted from an incident beam from the source of X-ray fluorescence striking the insulated structure;
- whereby the system is adapted for both detecting corrosion beneath the insulation and in the thickness of the insulated structure and for detecting corrosion beneath the insulation at the surface of the insulated structure.

* * * * *